United States Patent
Nikkels et al.

(10) Patent No.: US 7,299,683 B2
(45) Date of Patent: Nov. 27, 2007

(54) METAL PARTICLE SENSOR SYSTEM

(75) Inventors: Robert Ronald Nikkels, Gardnerville, NV (US); Sean Kelly Summers, Carson City, NV (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/276,592

(22) Filed: Mar. 7, 2006

(65) Prior Publication Data

US 2007/0209427 A1    Sep. 13, 2007

(51) Int. Cl.
*G01N 15/00*    (2006.01)
*G01N 33/20*    (2006.01)

(52) U.S. Cl. ............... 73/53.07; 73/61.42; 73/861.04

(58) Field of Classification Search ............. 73/53.05, 73/53.07, 61.41, 61.42, 861.04
See application file for complete search history.

(56) References Cited

U.S. PATENT DOCUMENTS

| | | | | |
|---|---|---|---|---|
| 2,760,184 A | * | 8/1956 | Beattle | 340/609 |
| 3,449,667 A | * | 6/1969 | Gourdine | 324/71.1 |
| 3,689,833 A | * | 9/1972 | Hogg | 324/71.1 |
| 4,909,081 A | * | 3/1990 | Kulczyk et al. | 73/597 |
| 5,041,856 A | * | 8/1991 | Veronesi et al. | 324/204 |
| 5,357,197 A | * | 10/1994 | Sorkin | 324/204 |
| 5,754,055 A | * | 5/1998 | McAdoo et al. | 324/636 |
| 5,760,298 A | * | 6/1998 | Fisher et al. | 73/61.42 |
| 5,789,661 A | * | 8/1998 | Fauque et al. | 73/37.5 |
| 5,932,795 A | * | 8/1999 | Koutrakis et al. | 73/28.01 |
| 5,968,371 A | * | 10/1999 | Verdegan et al. | 210/739 |
| 5,970,801 A | * | 10/1999 | Ciobanu et al. | 73/861.52 |
| 6,651,514 B2 | * | 11/2003 | Zanker | 73/861.52 |
| 6,895,808 B2 | * | 5/2005 | Remmlinger et al. | 73/53.07 |

FOREIGN PATENT DOCUMENTS

WO    WO 9400739 A1    *    1/1994

OTHER PUBLICATIONS

Janna, "Introduction to Fluid Mechanics," 2nd edition, 1987, PWS Publishers, 2nd edition, pp. 494-496.*
Gastops, "MetalSCAN On-Line Oil Debris Monitor", pp. 2.

* cited by examiner

*Primary Examiner*—Hezron Williams
*Assistant Examiner*—John Fitzgerald
(74) *Attorney, Agent, or Firm*—Sutherland, Asbill & Brennan LLP

(57) ABSTRACT

A metal particle sensor system for detecting metal particles in an oil line. The metal particle sensor system may include a metal particle sensor positioned about the line, an orifice positioned within the line and downstream of the metal particle sensor, a first pressure sensor positioned upstream of the orifice, and a second pressure sensor positioned downstream of the orifice. The metal particle sensor detects metal particles in the line while the first pressure sensor and the second pressure sensor determine a pressure drop across the orifice.

19 Claims, 2 Drawing Sheets

METAL PARTICLE SENSOR SYSTEM

TECHNICAL FIELD

The present application relates generally to the use of metal particle sensors and more particularly relates to a multiple sensor system for metal particles in an oil lubricant line.

BACKGROUND OF THE INVENTION

Ball bearings or gears used in many machines may have a finite lifetime. As these parts degrade, metal fragments and particles often end up in the lubricating oil stream. These particles can cause significant damage to the machine as a whole if not reduced or eliminated.

There are a number of metal particle sensors currently on the market to monitor metal particles in a lubricating oil line. The condition of the bearings or the gears can be extracted by determining how much of the metal has gone into the oil stream. Sensors can be placed in different locations to review the status of a single bearing or the status of an entire group. These measurements, however, tend to vary based upon the flow rate of the oil or the depth of the oil line and thus may provide inaccuracies. Such inaccurate measurements can lead or contribute to machine failure and/or a reduced lifetime.

Thus, there is a desire for an improved metal particle sensor device that can accommodate many different flow rates and oil lines. Such a device preferably would have a minimum impact on the machine as a whole, would be relatively small in size, would be simple to install, and would need little or no calibration. Such a device preferably would provide a constant and reliable output.

SUMMARY OF THE INVENTION

The present application thus describes a metal particle sensor system for detecting metal particles in an oil line. The metal particle sensor system may include a metal particle sensor positioned about the line, an orifice positioned within the line and downstream of the metal particle sensor, a first pressure sensor positioned upstream of the orifice, and a second pressure sensor positioned downstream of the orifice. The metal particle sensor detects metal particles in the line while the first pressure sensor and the second pressure sensor determine a pressure drop across the orifice.

The orifice provides a backfill in the line about the metal particle sensor. The metal particle sensor may be a ferrous metal particle sensor or a non-ferrous metal particle sensor. The metal particle sensor system further may include a second orifice positioned downstream of the second pressure sensor. The second orifice provides a backfill in the line about the second pressure sensor. The metal particle sensor system further may include a gooseneck positioned downstream of the second pressure sensor. The gooseneck provides a backfill in the line about the second pressure sensor. The metal particle sensor system further may include a microprocessor so as to determine the flow rate in the line based upon the pressure drop across the orifice.

The present application further describes a method for determining the extent of metal particles in an oil line. The method may include positioning a first orifice in the line, measuring the pressure drop across the orifice, determining the flow rate in the line based upon the pressure drop, and detecting the presence of metal particles in the line based upon the flow rate therethrough. The method further may include the steps of backfilling the line about the metal particle sensor, positioning a second orifice downstream of the first orifice, or positioning a gooseneck downstream of the first orifice.

The present application further describes a metal particle sensor system for detecting metal particles in an oil line. The metal particle sensor system may include a metal particle sensor positioned about the line to detect the metal particles, a first orifice positioned within the line and downstream of the metal particle sensor, a first pressure sensor positioned upstream of the first orifice, a second pressure sensor positioned downstream of the first orifice so as to determine the pressure drop across the first orifice, and a second orifice positioned downstream of the second pressure sensor.

The first orifice provides a backfill in the line about the metal particle sensor. The metal particle sensor may include a ferrous metal particle sensor or a non-ferrous metal particle sensor. The second orifice provides a backfill in the line about the second pressure sensor. The metal particle sensor system further may include a microprocessor so as to determine the flow rate in the line based upon the pressure drop across the orifice.

These and other features of the present application will become apparent to one of ordinary skill in the art upon review of the following detailed description when taken in conjunction with the drawings and the appended claims.

DETAILED DESCRIPTION

Figure 1:
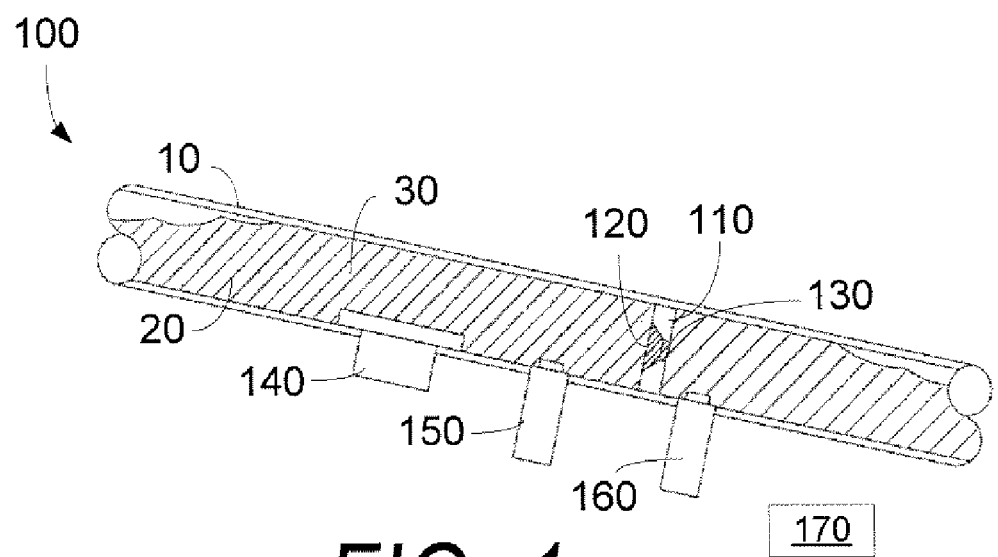
FIG. 1 is a side cross-sectional view of a metal particle sensor system as is described herein

Referring now to the drawings, in which like numerals refer to like elements throughout the several views. FIG. 1 shows a conventional lubrication line 10 with a lubricating oil 20 flowing therein. Any type of fluid may be used herein. Metal particles 30 may be dispersed within the flow of the oil 20.

FIG. 1 further shows a metal particle sensor system 100 as is described herein. The metal particle sensor system 100 may include a first orifice 110 positioned within the lubricating line 10. The first orifice 110 may be a conventional pressure drop device with an entrance 120 of a given area leading to an exit 130 of a reduced area. Any similar types of pressure drop devices may be used herein. The size of the entrance 120 and the exit 130 as well as orifice 110 as a whole may depend upon the average viscosity of the oil flow 20, the expected flow rate range, and the percentage range at full volume in the oil line 10. The use of the first orifice 110 not only provides the required pressure drop, but also helps backfill the volume of the oil flow 20 about the particle sensor 140. The orifice 110 also helps to remove air voids in the oil line 10.

The metal particle sensor system 100 further includes a metal particle sensor 140. The metal particle sensor 140 may be a conventional device that detects ferrous (FE) particles 30 such as iron and steel and/or non-ferrous (NFE) particles 30 such as aluminum, zinc, copper, and brass. Other types of materials may be detected herein. An example of such a particle sensor 140 is sold by Gastops and Momac Maschinebau GmbH Co. of Germany under the mark "METAL SCAN MS3000 SENSOR". Any type of similar detection device also may be used. The metal particle sensor 140 is positioned upstream of the first orifice 110.

The metal particle sensor system 100 further may include a pair of pressure sensors, a first sensor 150 and a second sensor 160. The sensors 150, 160 may be of conventional design. The first sensor 150 is positioned upstream of the first orifice 110 while the second sensor 160 is positioned downstream of the first orifice 110. Based upon the output of the sensors 150, 160, the pressure drop across the first orifice 110 can be determined according to the Bernoulli Obstruction Theory so as define the flow rate therethrough. Other types of calculations may be used herein.

The metal particle sensor system 100 thus determines the presence of the metal particles 30 via the particle sensor 140 and also determines the flow rate based upon the pressure drop through the first orifice 110 as determined by the sensors 150, 160. Thus, an accurate determination of the metal particle flow rate can be made. The pressure drop also can be used to ensure that the flow rate within the oil line 20 is acceptable and to ensure that the particle sensor 140 is working correctly.

The output of the metal particle sensor 140 and the first and second pressure sensors 150, 160 may be collected and evaluated via a convention microprocessor 170. The microprocessor 170 may provide output signals as appropriate. As described above, the microprocessor 170 likewise can determine the flow rate across the orifice 120 based upon the detected pressure drop. Likewise, communication interfaces (not shown) also may be used herein as desired.

Figure 2:
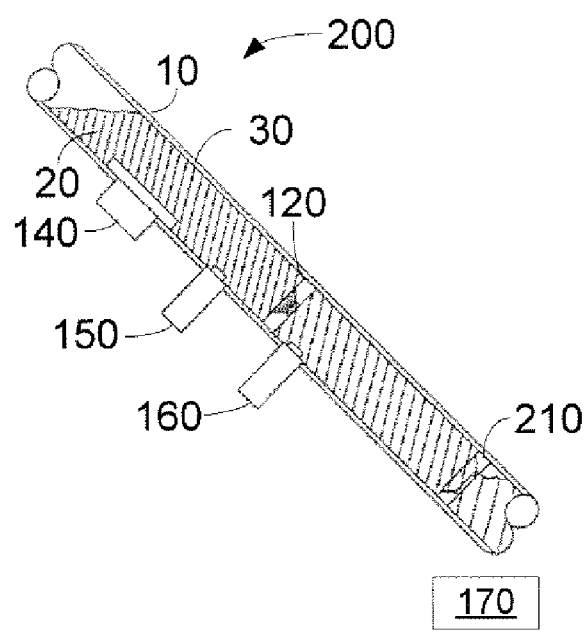
FIG. 2 is an alternative embodiment of a metal particle sensor system as is described herein.

FIG. 2 shows a further embodiment of a metal particle sensor system 200. The metal particle sensor system 200 is identical to the metal particle sensor system 100 but with the addition of a second orifice 210. The second orifice 210 may be positioned downstream of the first orifice 110 and the second sensor 160. Similar to the first orifice 110, the second orifice 220 helps backfill the oil line 20 about the second sensor 160. As described above, the size of the second orifice 210 may vary according to the average viscosity of the oil flow 20, the expected flow rate range, and the percentage range at full volume in the oil line 10.

Figure 3:
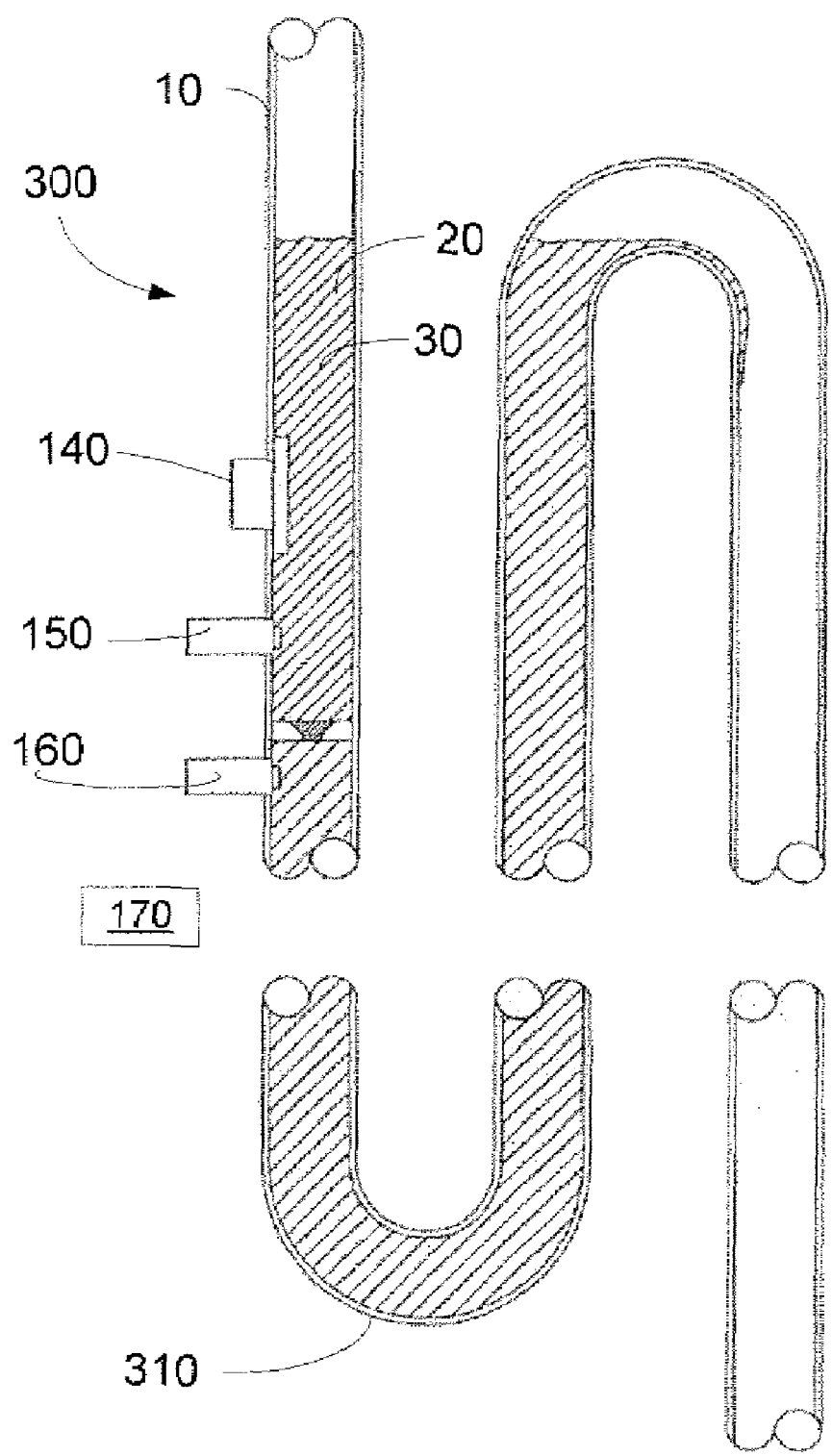
FIG. 3 is a further alternative embodiment of a metal particle sensor system as is described herein.

FIG. 3 shows a further embodiment of a metal particle sensor system 300. The metal particle sensor system 300 may be identical to the metal particle sensor system 100, but with the addition of one or more goosenecks 310 in the oil line 20 downstream of the second sensor 160. The gooseneck 310 acts in a manner largely identical to the second orifice 210 described above in the metal particle sensor system 200 so as to backfill the oil line 20 about the second sensor 160. Similar oil line orientations may be used herein.

It should be apparent that the foregoing relates only to the preferred embodiments of the present application and that numerous changes and modifications may be made herein by one of ordinary skill in the art without departing from the general spirit and scope of the invention as defined by the following claims and the equivalents thereof.

We claim:

1. A metal particle sensor system for detecting metal particles in an oil line, comprising:
    a metal particle sensor positioned about the line;
    an orifice positioned within the line and downstream of the metal particle sensor, the orifice providing a backfill in the line about the metal particle sensor;
    a first pressure sensor positioned upstream of the orifice; and
    a second pressure sensor positioned downstream of the orifice.

2. The metal particle sensor system of claim 1, wherein the metal particle sensor detects metal particles in the line while the first pressure sensor and the second pressure sensor determine a pressure drop across the orifice.

3. The metal particle sensor system of claim 1, wherein the metal particle sensor comprises a ferrous metal particle sensor.

4. The metal particle sensor system of claim 1, wherein the metal particle sensor comprises a non-ferrous metal particle sensor.

5. The metal particle sensor system of claim 1, further comprising a microprocessor so as to determine the flow rate in the line based upon the pressure drop across the orifice.

6. The metal particle sensor system of claim 1, further comprising a second orifice positioned downstream of the second pressure sensor.

7. The metal particle sensor system of claim 6, wherein the second orifice provides a backfill in the line about the second pressure sensor.

8. The metal particle sensor system of claim 1, further comprising a gooseneck positioned downstream of the second pressure sensor.

9. The metal particle sensor system of claim 8, wherein the gooseneck provides a backfill in the line about the second pressure sensor.

10. A method for determining the extent of metal particles in an oil line, comprising:
    positioning a first orifice in the line;
    measuring a pressure drop across the orifice;
    determining the flow rate in the line based upon the pressure drop; and
    detecting the presence of metal particles in the line based upon the flow rate therethrough.

11. The method of claim 10, further comprising the step of backfilling the line about a metal particle sensor.

12. The method of claim 10, further comprising the step of positioning a second orifice downstream of the first orifice.

13. The method of claim 10, further comprising the step of positioning a gooseneck downstream of the first orifice.

14. A metal particle sensor system for detecting metal particles in an oil line, comprising:
    a metal particle sensor positioned about the line to detect the metal particles;
    a first orifice positioned within the line and downstream of the metal particle sensor;
    a first pressure sensor positioned upstream of the first orifice;
    a second pressure sensor positioned downstream of the first orifice so as to determine a pressure drop across the first orifice; and
    a second orifice positioned downstream of the second pressure sensor.

15. The metal particle sensor system of claim 14, wherein the first orifice provides a backfill in the line about the metal particle sensor.

16. The metal particle sensor system of claim 14, wherein the metal particle sensor comprises a ferrous metal particle sensor.

17. The metal particle sensor system of claim 14, wherein the metal particle sensor comprises a non-ferrous metal particle sensor.

18. The metal particle sensor system of claim 14, wherein the second orifice provides a backfill in the line about the second pressure sensor.

19. The metal particle sensor system of claim 14, further comprising a microprocessor so as to determine the flow rate in the line based upon the pressure drop across the orifice.

* * * * *